United States Patent [19]

Snyder et al.

[11] Patent Number: 4,520,112

[45] Date of Patent: May 28, 1985

[54] ASSAY METHOD FOR ORGANIC CALCIUM ANTAGONIST DRUGS AND A KIT FOR SUCH AN ASSAY

[75] Inventors: Solomon H. Snyder; Robert J. Gould, both of Baltimore, Md.

[73] Assignee: The Johns Hopkins University, Baltimore, Md.

[21] Appl. No.: 473,622

[22] Filed: Mar. 9, 1983

[51] Int. Cl.$^3$ .......................... G01N 33/60; G01T 1/00
[52] U.S. Cl. .................................... 436/504; 436/804; 436/808; 436/815
[58] Field of Search ................ 436/504, 804, 808, 815

[56] References Cited

PUBLICATIONS

Murphy et al., Evr. J. Pharmacol 77 (1982) 201–202.
Murphy et al., Proc. Natl. Acad. Sci. USA 80 (1983) 860–864.
Gould et al., Proc. Natl. Acad. Sci. USA 79 (1982) 3656–3660.
McAllister et al., J. Pharmaceutical Sci., 65 (1976) 431–432.

*Primary Examiner*—Christine M. Nucker
*Attorney, Agent, or Firm*—Cushman, Darby & Cushman

[57] ABSTRACT

A method for measuring the level of organic calcium antagonist drug in a body fluid comprises preparing a mixture of a radioactive calcium antagonist drug, a body fluid containing a calcium antagonist drug and a calcium antagonist receptor material, measuring the radioactivity of the radioactive calcium antagonist drug bound to said calcium antagonist receptor material and deriving the concentration of the calcium antagonist drug in the body fluid from a standard curve indicating the concentration of calcium antagonist drug versus inhibition of binding of said radioactive calcium antagonist drug to said receptor sites caused by the calcium antagonist drug in said body fluid. A kit for measuring the level of an organic calcium drug comprises a receptacle containing a radioactive calcium antagonist drug, a calcium antagonist receptor material and a standard amount of a nonradioactive calcium antagonist drug.

16 Claims, 1 Drawing Figure

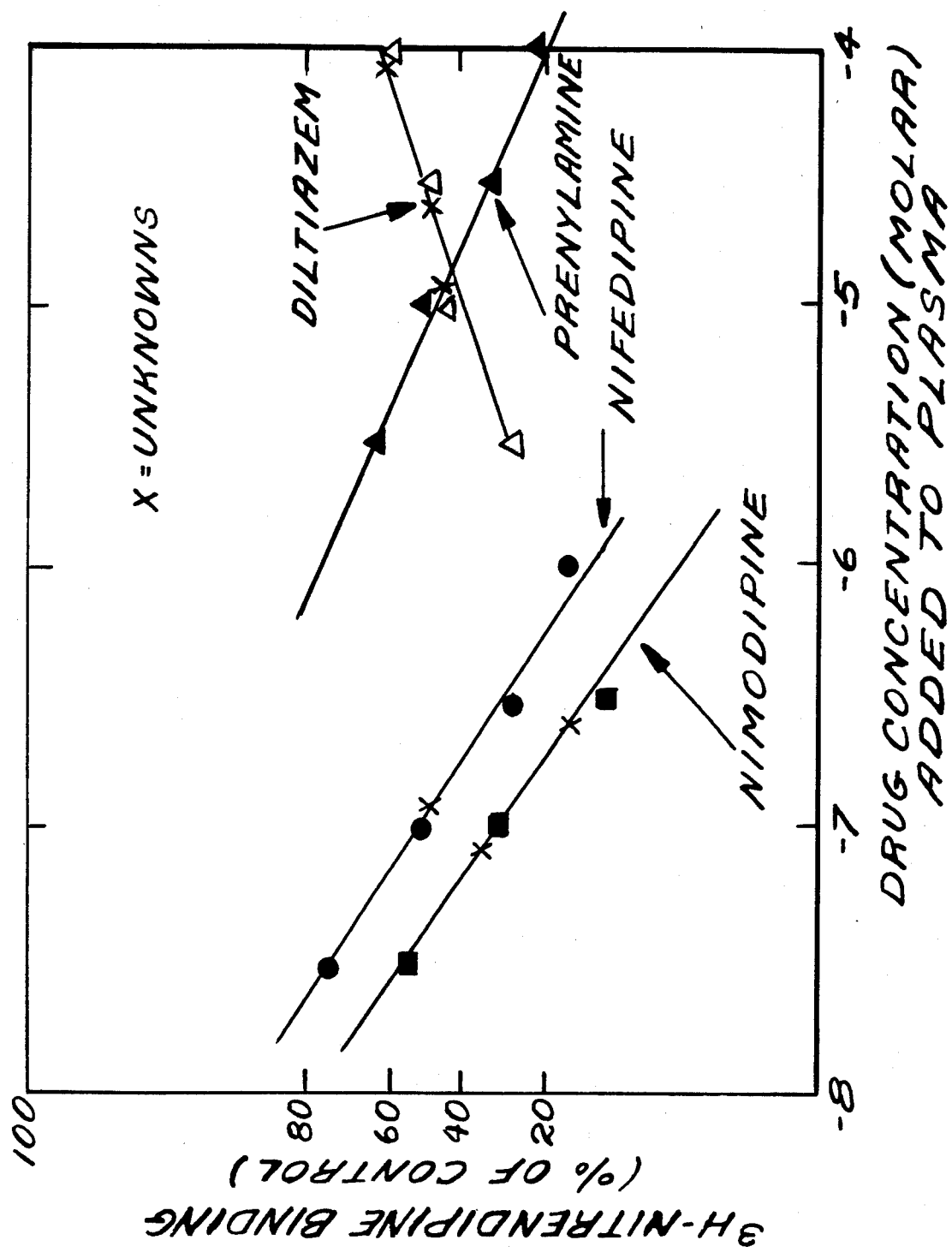

ASSAY METHOD FOR ORGANIC CALCIUM ANTAGONIST DRUGS AND A KIT FOR SUCH AN ASSAY

The invention described herein was made in the course of work under a grant or award from the Department of Health and Human Services.

BACKGROUND OF THE DISCLOSURE

During the past decade a number of drugs which are of therapeutic importance in treating various forms of cardiovascular disease have been developed and have been shown to exert their clinical effects by blocking voltage dependent calcium channels. There are several chemical classes of drugs which seem to act in somewhat different pharmacologic mechanisms. However, they all have in common the ability to block calcium channels. In the United States examples of three chemical classes of the drugs which are marketed commercially are respectively nifedipine, verapamil and diltiazem. These drugs are used extensively for treating angina pectoris and hypertension, but have also been evaluated for potential utility in treating numerous other medical conditions.

Dosage requirements for these drugs can vary considerably among different patients. In part the variable dose requirement is related to differences in absorption and metabolism of the drug among individuals. Attaining the optimal doses is important in securing maximal therapeutic benefit and avoiding potentially serious side effects of these drugs. It is generally felt that a simple and sensitive technique to measure these drugs in blood and other body tissues would facilitate selecting optimal doses.

Only three organic calcium antagonist drugs are currently marketed in the United States. Several others are already marketed in Europe and it is likely that within a few years there will be a substantial number in use throughout the world. Ideally, methods for measuring levels of these drugs in body fluids should be applicable to all the drugs. It is also possible that metabolites of some of the drugs may account for pharmacologic activity of the parent drug and so an ideal method should be able to measure pharmacologically active but not inactive metabolites in addition to the parent drug.

Presently available techniques include high performance liquid chromatography and radioimmunoassay. None of these techniques is used routinely in the clinic because of various technical diffuculties. Most of these techniques are applicable for individual drugs rather than for the whole class of calcium antagonists. Also such prior methods do not detect active metabolites.

In the past few years it has become possible to measure receptor sites where the organic calcium antagonist drugs exert their therapeutic actions. Receptors are measured by monitoring the binding of the radiolabeled form of a calcium antagonist drug to membranes from tissues that possess these receptors, including brain, heart, and skeletal muscle. Radioactive drugs that have been used to lable calcium antagonist receptors include $^3$H-nitrendipine (Murphy and Snyder, *Eur. J. Phamacol.*, 77:201–202, 1982; Gould, Murphy and Snyder, *Proc. Natl. Acad. Sci. USA*, 79:3656–3660, 1982; Bolger et al, *Biochem. Biophys. Res. Comm.*, 104:1604–1609, 1982; Ehlert et al., *Life Sci.*, 30:219–220, 1982; Belleman et al., *Drug Res.*, 32:361-363 1982) and $^3$H-nimodipine (Belleman et al., *Drug Res.*, 32:361-363, 1982). While the dihydropyridine calcium antagonists such as nifedipine compete directly for $^3$H-nitrendipine binding, drugs of other calcium antagonists classes, such as verapamil and diltiazem, interact allosterically with the same receptor site and also reduce $^3$H-nitrendipine binding (Yamamura et al., *Biochem. Biophys. Res. Comm.*, 108:640–646, 1982; Murphy, Gould, Largent and Snyder, *Proc. Natl. Acad. Sci., USA*, 1983, in press).

None of these publications or any other publications describing receptor binding for calcium antagonist drugs has disclosed anything beyond the fact that receptor sites for the calcium antagonist drugs can be measured with various radioactive forms of these drugs and that the drugs compete with the binding of these radioactive agents for the receptor.

Moreover, the information contained in the above mentioned publications does not provide a tool for measuring amounts of the calcium antagonist drugs in body fluids of human patients, because of a number of needed elements, all of which were yet to be discovered, had to be discovered for a successful assay for levels of the calcium antagonist drugs. For a successful assay for a calcium antagonist drug levels it was necessary to discover the nonspecific effects of body fluids on the binding properties of the calcium antagonist receptors and discover means of reducing or abolishing them. It was also necessary to discover that calcium antagonist drugs which added to body fluid could be recovered in a form that could still interact with the receptor sites. It was also necessary to show that in the presence of body fluids increasing amounts of the calcium antagonist drugs would in a predictable fashion produce progressively greater blockade of these receptors. Only after making a series of discoveries as disclosed herein, which reduced nonspecific effects of body fluids on the calcium antagonist receptors, permitted recovery of added calcium antagonist drugs and resulted in reproducible augmentations in receptor blockade with increasing amounts of calcium antagonist drugs in body fluids, was it possible to measure calcium antagonist drugs in body fluids with this invention.

BRIEF DESCRIPTION OF THE DISCLOSURE

The present invention is directed to a new technique which permits rapid determination of the concentration of calcium antagonist drugs in patients. Prior techniques for measuring levels of these drugs, as mentioned previously, are not generally applicable to all available calcium antagonist drugs and do not detect active but not inactive metabolites. Accordingly, a new and improved technique that could easily and rapidly be used was needed to ensure that patients were properly being dosed to achieve beneficial effects without causing harmful side effects.

The present invention provides such a technique and is based on the fact that calcium antagonist drugs will successfully compete with the binding of radioactive calcium antagonist drugs to receptor sites in such a manner that an accurate determination of concentrations of the calcium antagonist drugs in body fluids can be readily determined.

The present invention is also based in part upon the discovery that once the competition of radioactive calcium antagonist drug to receptor sites has proceeded for the desired time, the labeled drug and receptor can be successfully separated from free drug and receptor and bodily fluid without destroying the accuracy of the concentration measurement to be made.

After the separation the level of the calcium antagonist drug can be measured in any conventional radioactive measurement device, e.g. scintillation counter or gamma counter, depending on the radionuclide of the radioactive calcium antagonist drug, and compared to standard curves to determine concentration of the drug in a patient.

Thus, described herein is a method for measuring levels of calcium antagonist drugs, including levels of free drugs and active metabolites thereof, in patients based on the ability of these drugs to compete with the binding of radiocative calcium antagonist drugs (ligands) including organic calcium antagonist drugs of various subclasses such as the dihydropyridine, verapamil or diltiazem type classes to receptor sites in calcium antagonist receptor containing material. An active metabolite is a compound which itself acts as a calcium antagonist drug and is somehow formed in the patient (human) body from the drug directly or indirectly.

In this procedure increasing amounts of calcium antagonist drugs or active metabolites thereof decrease the binding of the radioactive ligand to the receptor site or reduce the inhibition of binding caused by an added standard drug. The biological fluid sample may be assayed without the separation of the calcium antagonist drug therefrom, e.g. blood serum or blood plasma may be directly assayed to determine the calcium antagonist blood level.

Suitable calcium antagonist receptor material is obtained from animal tissues enriched in these preparations such as the brain, heart, or skeletal muscle. Suitable receptor material is obtained from humans or from animals species such as bovine, or rodent (rat).

The calcium antagonist receptor material may be used as such or fractionated in a conventional manner to obtain fractions enriched in receptor containing membranes and may be washed or unwashed.

The calcium antagonist receptor material may preferentially be sold as a conventional freeze dried preparation in a test tube, e.g. coupled to the interior of the test tube so that the ligand and drug may be easily added to it.

As the radioactive ligand, radioactive labeled compounds such as $^3$H-nitrendipine or $^3$H-nimodipine or any other calcium antagonist drug may be used, provided that their binding to receptor sites can be measured.

In principle these compounds are conventionally labeled in a manner well known in the art with any radionuclide. Listing of the radionuclides which are now conventionally in use as reagents and which may be used in this invention are listed on page 160 of the 1979-80 catalog of the Amersham Radiochemical Company, Chicago, Ill., USA. Among radionuclides which are preferred in this invention the following may be mentioned:

hydrogen-3(tritium) and the radioisotopes of iodine (123-I, 124-I and 125-I, 126-I, 128-I, 130-I and 132-I) with 125-I and 131-I being preferred from considerations of availability, half-life, specific activity and the ability of radioactive iodine compounds to be readily measured using a conventional gamma counter usually available in hospitals.

In typical experiments the membranes containing the calcium antagonist receptor material can be incubated at various temperatures for various periods of time with appropriate ligand. Typically $^3$H-nitrendipine of high specific radioactivity purchased from the New England Nuclear Corporation in Boston, Mass. is incubated with rat or calf brain membranes in a buffer solution at a pH of 7.7 at a temperature of 25° for 45 mins and then filtered under vacuum through Whatman GF/B filters with two 5 ml rinses of cold buffer. The filters can be counted in liquid scintillation counters. Counting may also be accomplished using a gamma counter for 125-I ligands.

Specific binding to the calcium antagonist receptor is determined as the excess over the blank taken in the presence of 60 nM nefedipine though blanks can be obtained using a variety of the other agents that interact with calcium antagonist receptors. The ligand can be any calcium antagonist drug labeled with radioactivity.

Biological fluid samples, e.g. urine, blood plasma, blood serum, etc. supposedly containing calcium antagonist drugs are added to this assay. The biological samples can be added without any purification or may be subjected to purification procedures. Purification or concentration of biological fluid containing the calcium antagonist drug can employ any of numerous chemical techniques including solvent extraction, column chromatography, adsorption onto especially treated fibers or other chemical substance or by any other chemical procedure which may help purify or concentrate the calcium antagonist drug.

The amount of calcium antagonist drug is quantified by the extent to which it alters the binding of the labeled ligand to the receptor. The values can be expressed in any convenient units. The incubation mixture for the receptor binding can include any of numerous additives to facilitate binding or to protect the drugs or labeled ligands. The duration of the incubation can vary and involve any convenient time. Though, it is best to conduct the incubation to equilibrium, a suitable time for incubation could be anywhere from 2 mins to 4 hours, 45 mins being preferred. Receptor bound ligand can be trapped by filtration, centrifugation or any known technique which separates bound from unbound ligand.

Other suitable trapping techniques may also be used so long as they will permit the retention of the large size calcium antagonist receptor material having bound ligand while being able to separate the unbound ligand and free calcium antagonist drug. Other examples of suitable filter material include millipore filters of various sizes, e.g. 0.6 micron diameter holes. Preferably the calcium antagonist receptor material is buffered by a buffering solution such as Tris HCL Buffer sold by Sigma Laboratory, St. Louis, Mo., having a pH of 7.7. Other suitable buffering solutions include sodium phosphate buffer, glycine buffer and Hepes buffer and others which will provide the preferred pH (6-9) in the mixture to permit rapid binding of the radioactive labeled binder to the calcium antagonist receptor material. Thus this invention provides a new and improved method for determining concentrations in units of calcium antagonist drugs such as nifedipine, nimodipine, nitrendipine, verapamil, and diltiazem and others which are known in the art as competitors at calcium antagonist receptors.

In particular, the method is easily practiced by preparing a mixture of radioactive ligand, body fluid, e.g. blood serum, blood plasma or urine, and calcium antagonist receptor material, measuring the radioactivity (counts) of the ligand attached to the calcium antagonist receptor material preferably after separating unbound materials from the receptor and then deriving the concentration of the calcium antagonist from the standard curve which indicates the concentration of drug verus inhibition of the radioactive binding to the receptor caused by the calcium antagonist drug in the blood serum or plasma. For some drugs, such as diltiazem, using a ligand such as $^3$H-nitrendipine, one preferably measures the reversal of inhibition of $^3$H-nitrendipine binding by another drug such as tiapamil.

It has been discovered that the concentration of blood plasma or serum in the assay is most preferably no greater than 10% of the total assay volume of the ingredients in the test tube and preferably no more than 1%. Higher concentrations of plasma or serum inhibit the binding of $^3$H-ligands to calcium antagonist receptors even without drug present. Specifically we have found that 20 $\mu$l of normal human plasma per ml incubation mixture provides $^3$H-nitrendipine binding which is 60±1.2% of control values in the absence of plasma. This mean ±S.E.M. derives from 29 different subjects and indicates the very small variability among subjects. With 10 $\mu$l plasma per ml incubation values are 90% of control levels with the same small variability. In routine assays 10 $\mu$l of plasma are diluted in 1 ml incubation volume. The sensitivity of the technique is such that normal therapeutic plasma levels of calcium antagonist drugs will be detected following this dilution. This provides an important discovery necessary to permit measuring calcium antagonists blood levels for the following reasons. (1) The dilution of the sample causes drug bound to plasma protein to dissociate so that total plasma levels can be measured. (2) The inhibition of $^3$H-nitrendipine binding by 10 $\mu$l of plasma is small enough that drug levels can be measured reliably. (3) The minimal variability between individual plasma samples in reducing $^3$H-nitrendipine binding further establishes the reliability of monitoring $^3$H-nitrendipine binding to evaluate blood levels of calcium antagonist drugs. Even if plasma inhibited binding only 10% on average, but some subjects gave 40% inhibition while others gave zero inhibition, then one could not reliably measure blood levels of calcium antagonist drugs.

In addition this invention provides a new composition of matter comprising radioactive ligand, calcium antagonist drug and calcium antagonist receptor material and blood serum or plasma in a kit as a mercantile unit comprising at least one container containing the following ingredients: calcium antagonist receptor material, radioactive ligand for these receptor materials, and a standard amount of nonradioactive calcium antagonist drug. Each of these ingredients may also be packaged in one or more individual containers.

EXAMPLE I

The following example illustrates measurement of blood plasma nifedipine, nimodipine, prenylamine and diltiazem levels:

Materials

I. Calcium Channel Receptor:

Cerebral cortex membranes were used as a source of calcium channel receptors. One bovine brain was obtained from a local abattoir and the cortex was immediately dissected. One hundred g of cortex were homogenized in 1 liter of ice-cold 50 mM Tris-HCl buffer, pH 7.7 with a Brinkman polytron (setting 7) for 30 sec. The homogenate was then divided into 50 equal portions and centrifuged at 4° C. for 10 minutes at 40,000×g in Sorvall RC5B centrifuge. The resulting pellets were homogenized in 20 ml of the ice-cold Tris buffer as previously described and centrifuged at 40,000 ×g for 10 minutes. The pellets were again homogenized, as previously described, in 20 ml of ice-cold 50 mM Tris HCl, pH 7.7 and frozen at −70° C. until use. When used, homogenates were thawed and adjusted to a final volume of 400 ml by adding 380 ml of ice-cold 50 mM Tris HCl pH 7.7.

II. Calcium Channel Antagonist Standards:

A. Six nifedipine standards were prepared by dissolving varying concentrations of nifedipine in pooled human plasma as follows:

1. $2.5 \times 10^{-5}$ M nifedipine in human plasma
2. Human plasma with no added nifedipine
3. $1 \times 10^{-7}$ M nifedipine in human plasma
4. $3 \times 10^{-7}$ M nifedipine in human plasma
5. $1 \times 10^{-6}$ M nifedipine in human plasma
6. $3 \times 10^{-6}$ M nifedipine in human plasma.

B. Six nimodipine standards were prepared by dissolving varying concentration of nimodipine in pooled human plasma as follows:

1. same as A1
2. same as A2
3. same as A3
4. same as A4
5. same as A5
6. same as A6.

C. Six prenylamine standards were prepared by dissolving varying concentrations of prenylamine in pooled human plasma as follows:

1. same as A1
2. same as A2
3. $1 \times 10^{-5}$ M prenylamine in human plasma
4. $3 \times 10^{-5}$ M prenylamine in human plasma
5. $1 \times 10^{-4}$ M prenylamine in human plasma
6. $3 \times 10^{-4}$ M prenylamine in human plasma.

D. Six diltiazem standards were prepared by dissolving varying concentrations of diltiazem in pooled human plasma as follows:

1. same as A1
2. same as A2
3. same as C3, plasma contained 50 $\mu$M tiapamil
4. same as C4, plasma contained 50 $\mu$M tiapamil
5. same as C5, plasma contained 50 $\mu$M tiapamil
6. same as C6, plasma contained 50 $\mu$M tiapamil As used herein human plasma means human blood plasma.

III. Unknown:

Nifedipine, nitrendipine, prenylamine, diltiazem dissolved in human plasma.

IV. Labelled Ligand:

($^3$H-nitrendipine) (75 Ci/mmol) obtained from New England Nuclear was diluted in 50 mM Tris HCl pH 7.7 to give 10,000 cpm/25 $\mu$l.

V. Assay Procedure:

The assay is performed in 12×75 mm glass test tubes. Standard and unknown samples are assayed in triplicate. To each tube the following additions are made in order: 20 $\mu$l of calcium channel antagonist standard or 20 $\mu$l of unknown, 25 $\mu$l of labeled ligand, 1 ml of calcium channel receptor cerebral cortical membranes. The tubes are then mixed with a vortex mixer and incubated at room temperature for 30–60 mins. After this incubation, the contents of tubes are rapidly filtered with suction through Whatman GF/B glass fiber filters which have been placed in a Brandel filtration manifold. The filters are rapidly washed four times with 2 ml of 50 mM Tris HCl, pH 7.7. The filters are then placed in 7.5 ml of NEN 947 in 20 ml liquid scintillation vials. After 0.5 hr of shaking, the filters are counted for 2 minutes in a liquid scintillation counter using a $^3$H-window setting (LKB Spectrometer).

VI. Calculation of results:

The average counts per minute for each set of triplicates is obtained. The average minus background counts per minute is computed.

TABLE 1

EFFECT OF HUMAN PLASMA ON $^3$H—NITRENDIPINE BINDING
Inhibition of $^3$H—Nitrendipine Binding
By 10 Microliters Human Plasma

|  | DAY 1 | DAY 2 |
|---|---|---|
|  | 16.8 | 16.7 |
|  | 16.0 | 11.6 |
|  | 15.7 | 4.5 |
|  | 14.5 | 1.3 |
|  | 11.4 | 0 |
|  | 20.1 | 0 |
|  | 23.7 | 9.6 |
|  | 14.1 | 5.2 |
|  | 26.1 | 4.0 |
|  | 15.9 | 0 |
|  | 12.9 | 0 |
|  | 13.6 | 0 |
|  | 23.9 | 22.5 |
|  | 25.5 | 11.7 |
|  | 19.3 | 13.6 |
|  | 15.2 | 14.2 |
|  | 19.8 | 9.1 |
|  | 31.9 | 18.1 |
|  | 28.2 | 17.7 |
|  | 14.5 | 5.6 |
|  | 12.4 | 5.2 |
|  | 11.4 | 3.9 |
|  | 14.5 | 3.6 |
|  | 0 | 2 |
|  | 17.9 | 14.5 |
|  | 9.7 | 15.9 |
|  | 0 | 20.9 |
|  | 7.1 | 18.1 |
|  | 4.4 | 11.7 |
| Number of Samples | 29 | 29 |
| Mean ± | 15.7 | 8.9 |
| SEM | 1.4 | 1.3 |
| Range | 0–31.9 | 0–22.5 |

Normal unmedicated adult male or female human plasma was employed. Samples of 10 microliters were added to incubations with $^3$H-nitrendipine as described in Assay Procedure. To assess the reproducibility of plasma effects, plasma samples from each subject were assayed on two consecutive days (day 1 and 2).

Drug concentrations were measured as described in Assay Procedure. Nimodipine, nifedipine and prenylamine were quantified on the basis of inhibition of $^3$H-nitredipine binding. Diltiazem was assayed by reversal of tiapamil induced reduction in $^3$H-nitrendipine binding. "Unknown" samples consisted of plasma with various drugs added. The coincidence of unknown values with the standard curve supports the reliability of the assay, as can be seen in the drawing.

What is claimed is:

1. A method for measuring the level of an organic calcium antagonist drug including a pharmacologically active metabolite thereof in a body fluid comprising
   (a) preparing a mixture of a radioactive calcium antagonist drug, a body fluid containing a calcium antagonist drug and a calcium antagonist receptor material having receptor sites whereby said calcium antagonist drug competes with the binding of said radioactive calcium antagonist drug to said receptor sites,
   (b) measuring the radioactivity of the radioactive calcium antagonist drug bound to said calcium antagonist receptor material, and
   (c) deriving the concentration of the calcium antagonist drug in said body fluid from a standard curve indicating the concentration of calcium antagonist drug versus inhibition of binding of said radioactive calcium antagonist drug to said receptor sites caused by the calcium antagonist drug in said body fluid.

2. The method of claim 1 wherein prior to measuring the radioactivity in step (b) the mixture resulting from step (a) is treated to remove therefrom any unbound radioactive calcium antagonist drug and calcium antagonist drug.

3. The method of claim 1 where in step (a) said mixture is incubated at a temperature and for a time sufficient to permit binding of said radioactive calcium antagonist drug and said calcium antagonist drug to said receptor sites.

4. The method of claim 3 wherein said mixture is incubated at ambient temperature for a period ranging from 2 minutes to 4 hours.

5. The method of claim 1 wherein the mixture in step (a) is buffered to a pH ranging from 6 to 9.

6. The method of claim 1 wherein said body fluid is present in the mixture of step (a) in an amount not greater than 10 percent of the total volume of said mixture.

7. The method of claim 1 wherein said body fluid is present in the mixture of step (a) in an amount not greater than 1 percent of the total volume of said mixture.

8. The method of claim 1 wherein said calcium antagonist receptor material is obtained from animal tissue.

9. The method of claim 8 wherein said tissue is brain, heart or skeletal muscle.

10. The method of claim 8 wherein said tissue is human tissue.

11. The method of claim 8 wherein the tissue is bovine or rodent tissue.

12. The method of claim 1 wherein the radioactive calcium antagonist drug is $^3$H-nitrendipine or $^3$H-nimodipine.

13. The method of claim 1 wherein said body fluid is urine, blood plasma or blood serum.

14. The method of claim 13 wherein the body fluid is purified so as to concentrate the calcium antagonist drug contained therein.

15. The method of claim 1 wherein said calcium antagonist drug is nifedipine, nimodipine, nitrendipine, verapamil, prenylamine or diltiazem.

16. A kit for measuring the level of an organic calcium antagonist drug, including a pharmacologically active metabolite thereof, in a body fluid, said kit comprising at least one receptacle containing one or more of a radioactive calcium antagonist drug, a calcium antagonist receptor material and a standard amount of a nonradioactive calcium antagonist drug.

* * * * *